United States Patent [19]

Schmidt et al.

[11] Patent Number: 5,339,826

[45] Date of Patent: Aug. 23, 1994

[54] METHOD FOR TRAINING MATERIAL EVALUATION WITH METHOD OF EEG SPECTRAL ESTIMATION

[75] Inventors: Albert L. Schmidt, Murrysville; Ellen K. McKinley, Monroeville; Lewis F. Hanes, Pittsburgh, all of Pa.; Michael R. Morris, Finksburg; Patrick J. McKenzie, Sykesville, both of Md.; Paul H. Haley, Monroeville, Pa.

[73] Assignee: Westinghouse Electric Corp., Pittsburgh, Pa.

[21] Appl. No.: 810,097

[22] Filed: Dec. 9, 1991

[51] Int. Cl.⁵ ............................................. A61B 5/0484
[52] U.S. Cl. ....................................................... 128/731
[58] Field of Search ................................. 128/731–732

[56] References Cited

U.S. PATENT DOCUMENTS

| | | | |
|---|---|---|---|
| 3,780,724 | 12/1973 | John | 128/731 |
| 4,332,566 | 1/1982 | Mazeski et al. | 128/732 X |
| 4,955,388 | 9/1990 | Silberstein | 128/731 |
| 5,024,235 | 6/1991 | Ayers . | |
| 5,137,027 | 8/1992 | Rosenfeld | 128/745 |

OTHER PUBLICATIONS

Assessing The Effectiveness of Video-Taped Training Materials Using Electroencephalographic (EEG) Measures.
U.S. patent application Ser. No. 07/228,136 entitled: Method and Apparatus For Physiological Evaluation of Short Films And Entertainment Materials.
Charles Shagass, "Electrical Activity of the Brain", *Handbook of Psychophysiology*, pp. 263–328.
H. Ehrlichman and M. S. Wiener, "EEG Asymmetry During Covert Mental Activity", *Psychophysiology*, vol. 17, No. 3, pp. 228–235.
D. Galin and R. Ornstein, "Lateral Specialization of Cognitive Mode: An EEG Study", *Psychophysiology*, pp. 412–418.
L. R. Warren, L. Peltz and E. S. Haueter, "Patterns of EEG Alpha During Word Processing and Relations to Recall", *Brain and Language*, pp. 283–291.
H. J. Neville, M. Kutas, G. Chesney, A. L. Schmidt, "Event-Related Brain Potentials during Initial Encoding and Recognition Memory of Congruous and Incongruous Words", *Journal of Memory And Language*, pp. 75–92.
E. Donchin, D. Karis, T. R. Bashore, M. G. H. Coles, G. Gratton, "Cognitive Psychophysiology and Human Information Processing" *Psychophysiology Systems, Processes, and Applications*, pp. 244–267.
M. J. Hannafic and K. L. Pecko, *The Design, Development and Evaluation of Instructional Software*, "Evaluating and Revising CAI Lessons", pp. 295–325 Macmillan Publishing Company, New York, 1988.

*Primary Examiner*—Angela D. Sykes

[57] ABSTRACT

The invention is a method and apparatus in which student EEG measurements are made during the videotaped presentation of training materials. Alpha (8–12 Hz) and beta (16–24 Hz) activity present during segments of the material directed to a learning objective are used to determine attention and cognitive activity during the training material. An increased level of attention relates to increased understanding of the material. An increased level of cognitive activity relate directly to incorrect understanding of the material. Evoked potential responses are also measured in response to multiple choice questions on the learning objections presented subsequent to the training materials. A difference between midterm responses for correct and incorrect answers measures correct understanding of the subject matter of the multiple choice question. Comparing the alpha, beta and evoked potential results for a learning objective validates the indication of effectiveness if the results correlate. To evaluate the EEG spectra for varying length recorded signal segments and between individuals with different magnitude responses, the EEG signals are normalized and interpolated to the same length before a windowed FFT is performed the peaks in the FFT are then found.

7 Claims, 12 Drawing Sheets

METHOD FOR TRAINING MATERIAL EVALUATION WITH METHOD OF EEG SPECTRAL ESTIMATION

CROSS REFERENCES TO A RELATED PATENT

This application is related to U.S. Pat. No. 5,243,517 filed Aug. 3, 1988 and entitled "METHOD AND APPARATUS FOR PHYSIOLOGICAL EVALUATION OF SHORT FILMS AND ENTERTAINMENT MATERIALS" incorporated by reference herein.

BACKGROUND OF THE INVENTION

1. Field of the Invention

The present invention is directed to determining the effectiveness of training materials using electrophysiological measures and, more particularly to a method and apparatus for determining the effectiveness of videotaped training materials using measurements of electroencephalographic (EEG) and evoked potential (EP) activity in the brain without using paper and pencil tests where the spectra of the EEG can be computed and compared between signals of different lengths for different people.

2. Description of the Related Art

Conventionally, teaching materials such as videotapes are evaluated using paper and pencil tests. That is, after an educational videotape or teacher presentation is presented to one or more students, the students are tested using standard pencil and paper tests to determine how much the students have learned. The student grades determine how much the students have learned and the effectiveness of the teaching materials. However, paper and pencil tests are subjective in that people can guess the answers or use various test taking strategies that distort the score.

SUMMARY OF THE INVENTION

It is an object of the present invention to provide objective evaluation of test materials.

It is another object of the present invention to evaluate test materials physiologically using signals produced by the brain of the subject.

It is also an object of the present invention to evaluate test materials without paper and pencil.

It is an additional object of the present invention to provide at least two measures for effectiveness evaluation that are independent to validate the or verify the accuracy of the measures.

It is a further object of the present invention to allow electroencephalographic (EEG) spectral estimation and comparison of EEG signals of varying length and from different individuals.

The above objects can be accomplished by a first method and apparatus in which student EEG measurements are made during the presentation of training materials and alpha and beta activity are used to determine attention and cognitive activity during the training material. The level of attention and the level of cognitive activity relate directly to correct understanding of the material by the student. Using a second apparatus and method, evoked potential responses are measured in response to multiple choice questions presented subsequent to the training materials. A difference between midterm responses for correct and incorrect answers measures correct understanding of the subject matter of the multiple choice question. The two independent methods validate the measurement of the effectiveness of the training materials. To evaluate the EEG spectra for varying length recorded signal segments during the first method and between individuals with different magnitude responses, the EEG signals are normalized and interpolated to the same length before a windowed FFT is performed after which the peaks are found in the spectrum.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
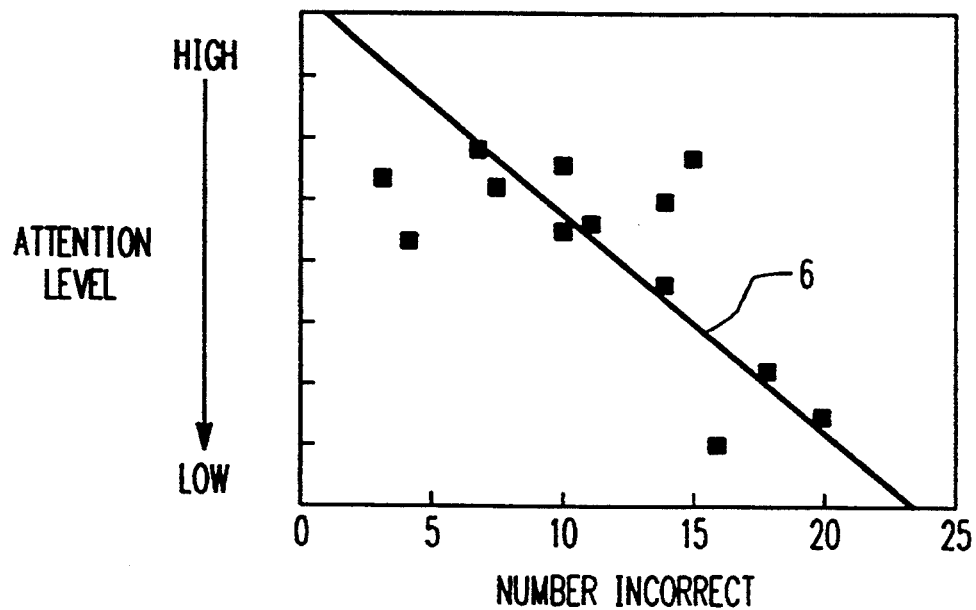
FIG. 1 illustrates the correlation between electroencephalographic (EEG) alpha activity and correct answers to test questions on a training material subject.

The present invention is directed to a system that applies independent electrophysiological measures, electroencephalographic (EEG) responses and evoked potential responses, to the evaluation of training materials, such as videotaped instruction and video disk computer based instruction although the invention could be used to evaluate the effectiveness of live training material presentations. EEG measures are recorded during the presentation of the training material. The EEG responses measure the attention and cognitive activity associated with the contents of the instruction. Attention and cognitive activity have been discovered by the inventors to correlate with knowledge about the materials presented. Event related potentials or evoked potentials (EP) measures are recorded during the administration of the evoked potential multiple choice test questions. A different type of EP response to a correct answer presented to a student results when the student has learned the subject matter versus a student who has not learned the subject matter. This difference in response correlates with knowledge about the materials presented. As a result, the present invention provides independent, cross verifiable methods for evaluating the effectiveness of training materials without the use of paper and pencil tests. Another advantage of the electrophysiological measures is that the measures do not require a behavioral response by the student. For this reason they are objective measures, that is, they are not contaminated by guessing and various test taking strategies.

There are two types of electrical brain responses that are used by the present invention to evaluate training materials. The first is EEG activity which is the continuous, electrical activity of the brain. EEG is sensitive to the specific type of task in which the subject is engaged. Specific frequencies of the EEG, for example, activity between 8-12 hertz (alpha activity) an activity between 16 and 24 hertz (beta activity) are sensitive to specific types of cognitive activity. Alpha activity measures the intake or rejection of environmental stimuli and can be thought of reflecting attention to the objects or events in the environment, in the present situation, the training material. Beta activity measures cognitive activity, that is, cognitive demand. By recording EEG activity during the presentation of the training material, the segments of the training tape which show low or high attention and cognitive levels can be identified. Such low or high attention and cognitive levels correlate directly to answers to subject matter questions presented in traditional paper and pencil tests. That is, different levels of attention and cognitive activity during the training materials are directly predictive of future performance on paper and pencil tests. Given that paper and pencil tests measure learning, measuring attention and cognitive levels provides a measure of learning.

Evoked potentials (EP), a second type of electrical brain response used to evaluate training materials is different and independent of EEG measures in that an evoked potential is a brain response that is time locked to a specific event in the environment. For example, a brief flash of light or the presentation of a picture or word results in a predictable electrical brain response. EEG measures can be thought of as reflecting general attention or cognitive activity, while an evoked potential (EP) response is a more specific measure of the perceptive/cognitive response associated with a specific event or stimuli. The EP is sensitive to memory processes and the degree to which a word is understood and the salience of a stimulus. EP measures also provide an accurate index of knowledge, more accurate than current paper and pencil tests.

Figure 2:
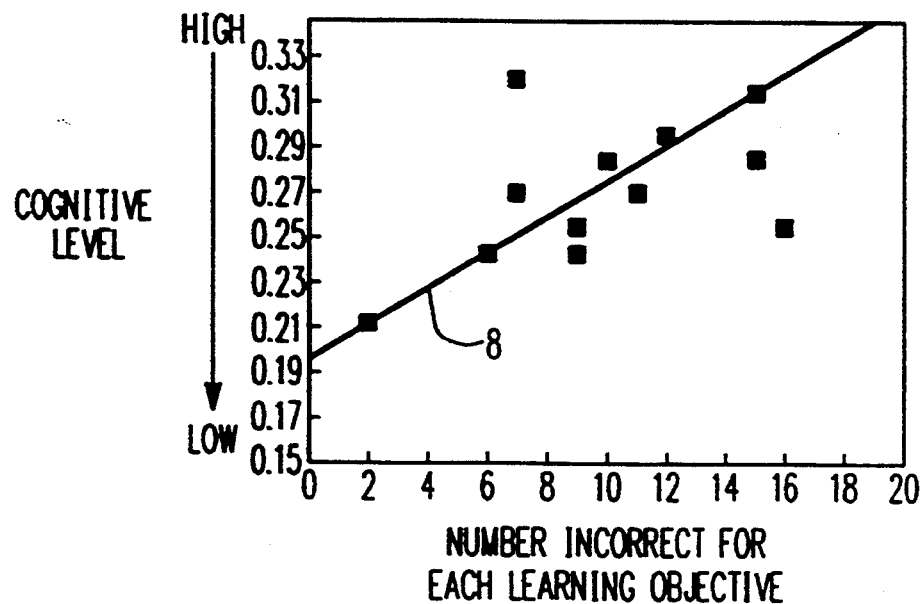
FIG. 2 illustrates the correlation between EEG beta activity and correct answers to test questions on a training material subject.

In tests conducted by the inventors hereof, EEG activity of a subject was recorded during the presentation of a training tape. The amplitude of the EEG activity in the alpha (attention) band and the beta (cognitive) band was measured for each learning objective on the tape and for the entire tape. The ratio of alpha and beta activity during the training tape to baseline alpha and beta activity recorded with the subject's eyes closed was calculated. The ratio of these EEG measures correlates with the performance of the subject on a paper and pencil test that was given after the training tape was presented. Attention was negatively correlated with the number of incorrect answers, that is, as attention increased, the number of incorrect answers decreased. As a result, the level of the alpha activity during the presentation of the training material on the learning objective is a direct measure of whether the person will correctly answer a question about that learning objective. This relationship between the attention and the number of incorrect answers is illustrated in FIG. 1. Cognitive activity is positively related to the number of incorrect answers, that is, as cognitive activity increases, the number of incorrect answers increases. Cognitive activity is a direct measure of the understanding of the subject concerning a particular learning objective. The relationship between a cognitive score for each learning objective and the number of incorrect answers is illustrated in FIG. 2. Since low attention levels and high cognitive levels are associated with incorrect answers on paper and pencil tests, learning materials that are associated with low attention and high cognitive levels can be identified and then modified to increase their effectiveness. Effectiveness can be enhanced by increasing the attention or interest generating level of the test materials for the learning objective and decreasing the cognitive demand of the learning objective by providing more simple explanations with respect to the learning objectives.

Figure 3A:
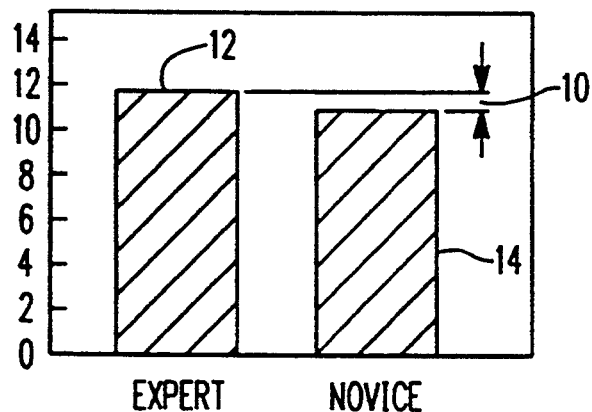
FIGS. 3A-3B and 4A-4B illustrate how evoked potential change correlates with knowledge about a training materials subject.
Figure 3B:
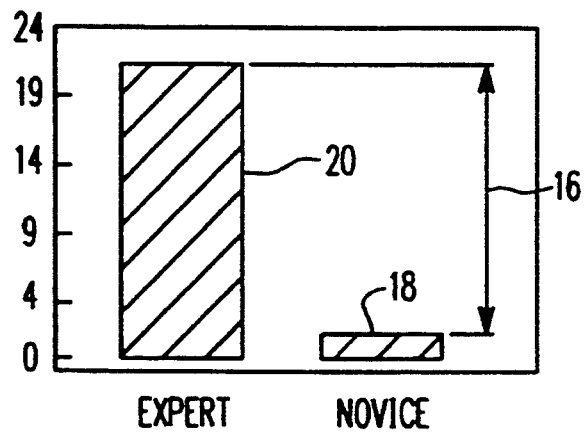
Figure 4A:
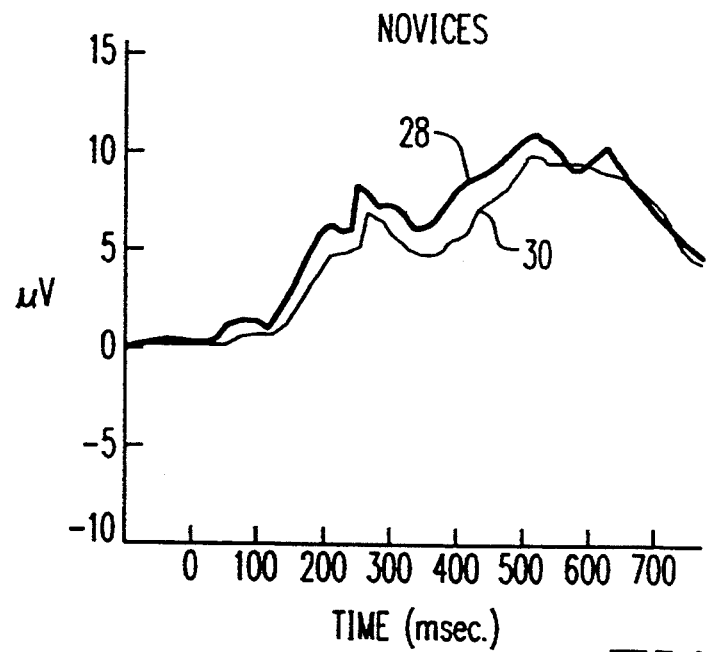
Figure 4B:
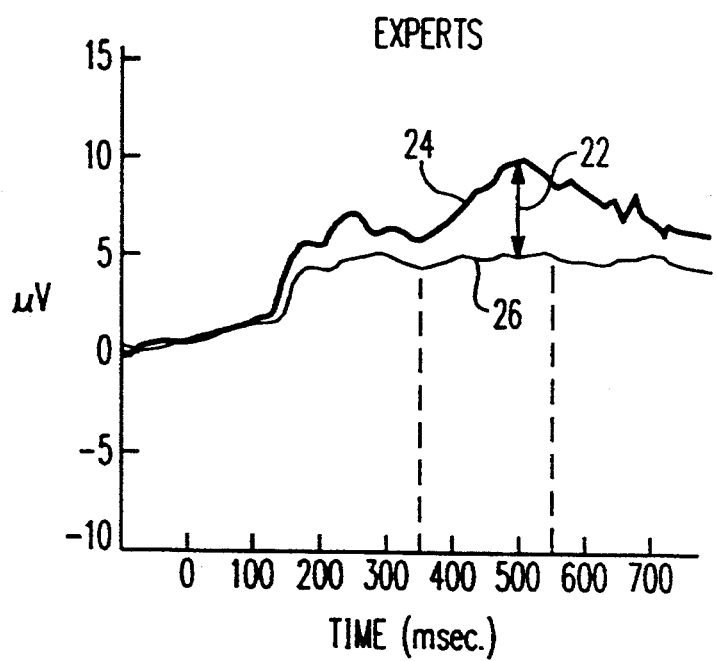

In a second test performed by the inventors, evoked potential responses to a multiple choice test question were recorded. This test was administered to a group of experts and a group of novices. The experts were experienced in the domain of the training tape and the test was given both as an evoked potential test and a paper pencil test. Results for these two versions are presented in FIGS. 3A and 3B. As can be seen, there is little difference in 10 test answers 12 and 14 between known experts and known novices on the paper and pencil version of the test and a large difference 16 in the evoked potential responses 18 and 20. The evoked potential results represent the percent change between all of the correct and incorrect alternatives. Examples of the actual, typical evoked potentials are presented in FIGS. 4A and 4B. These analyses show a disassociation between the performance on a paper and pencil test and the EP results on the same test. The EP test is able to discriminate a group of experts from a group of novices while the paper and pencil test did not. That is, an EP test is better able to discriminate among students that have a better understanding of the training material from students who do not. Of particular interest in the comparison of FIGS. 4A and 4B is the difference 22 in response to correct 24 and incorrect 26 alternatives in the EP test for experts at around 350-550 milliseconds as compared to the lack of difference in correct 28 and incorrect 30 response for novices. That is, if a peak with a substantial difference occurs in an evoked potential response to the correct 24 as opposed to the incorrect 24 alternatives for a multiple choice question, as illustrated in FIG. 4B, then this person is identified by this difference as a person with better understanding of or an expert in the subject matter of the question. Such a response difference does not occur for novices, as illustrated in FIG. 4A. That is, when a student shows the marked response difference at around 500 milliseconds demonstrated by experts, the student demonstrates understanding of the subject matter.

Figure 5:
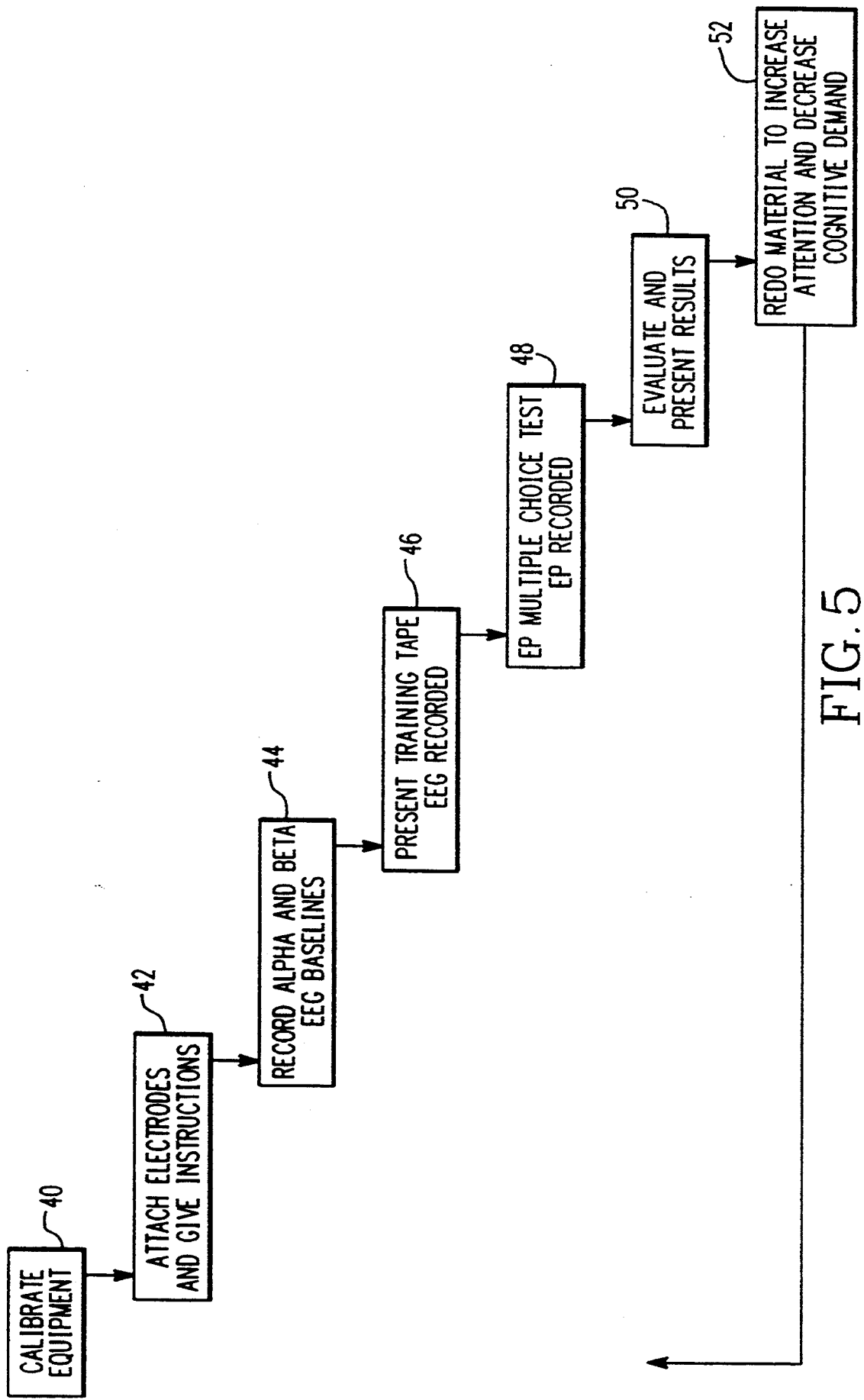
FIG. 5 illustrates the test procedure of the present invention.

The test procedure of the present invention is illustrated in FIG. 5. During a test or evaluation of the training material the forty subjects should include an even mix of both experts and novices, and the novices should be people that are to be trained in the subject matter. Each subject should be used separately if possible. The first step 40 of the evaluation is to calibrate the equipment which is performed in a manner as discussed in the related U.S. patent application previously mentioned. The next step is to attach the electrodes and give the student's their instructions. For example, telling the students that a training tape on a particular subject is being presented, that their objective is to learn as much about the subject as possible from the training tape and that a series of multiple choice questions will be presented subsequent to the training tape. The third step is to record 44 the alpha and beta EEG baselines where the alpha baseline is recorded by recording the EEG for 30 seconds while the subject's eyes are closed and the beta baseline is performed by recording the EEG for 30 seconds while the subject is counting backwards from some large number such as 1000 by an arbitrarily difficult number such as 3. Once the baselines are recorded the training tape is presented 46 and the EEG is recorded during the training tape presentation. Next, the ERP multiple choice test is given 48 and the ERPs are recorded in the same manner as described in the related U.S. patent application and is described in detail with respect to FIG. 14 and the price or value test described therein. This test involves presenting a fill in the blank statement, e.g. "An object that reflects energy back to the receiver from the transmitter is called a ___." Followed by four alternatives, such as "doppler, radar, target, radio." The statement is presented for 4 seconds followed by 1 second during which the screen was blank. A rectangle then appears followed 2 seconds later by the alternatives. Each alternative is presented individually for a duration of 150 msec. The time between alternatives is 2 seconds. An ERP is recorded to each alternative. Each statement and corresponding alternatives is presented four times. The subject is instructed to mentally recognize or detect the correct alternative. Once all of the data has been recorded, the data is evaluated 50 and the results are presented. By comparing the results produced by the EEG evaluation for a particular learning objective with the EP results for that same objective, the effectiveness of the learning material can be validated. Correlated results indicate validation of the results. The results provide an objective evaluation of the effectiveness of the training material. It is then possible to redo the training material to increase attention, decrease cognitive demand and simplify difficult areas. The training material can again be evaluated. By continuing this testing and modification, the training material can be fine tuned to maximize the effectiveness thereof.

Figure 6:
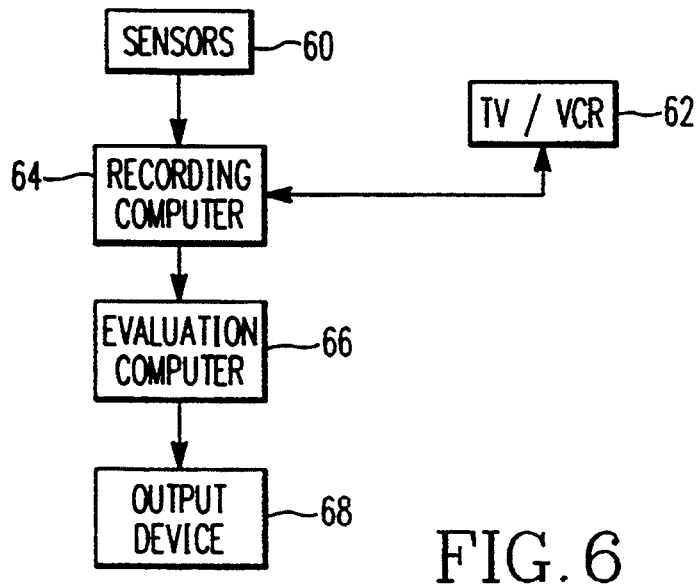
FIG. 6 is a block diagram of the hardware of the present invention.

The hardware of the present invention, as illustrated in FIG. 6, includes a television/VCR unit 62 which shows the training material to a subject (not shown) and also provides the multiple choice test questions to the subject. Sensors 60 attached to the subject's head sense the EEG and EPs produced by the subject during the training materials and the multiple choice tests. These sensors 60 provide the sensed signals to a recording computer 64 which also monitors sequencing and control signals on the videotape being played by the TV VCR unit 62. The recording computer 64 provides the EEG and EPs to an evaluation computer 66 which performs the evaluations discussed herein and produces an output to an output device 68 such as a printer or plotter. Additional details with respect to the hardware depicted in FIG. 6 can be found in the related U.S. patent application previously mentioned.

As previously mentioned the evoked potential is recorded for each of the answers to a particular question on the multiple choice test and the difference between the EP for the correct answer and the incorrect answers is used to determine whether the subject has become qualified in the subject of the learning objective to which the question is directed. The recording of the EP which occurs is performed as discussed in detail in the related U.S. patent application mentioned previously and is described in detail with respect to FIG. 23 therein. The determination of the EP magnitudes in the 350–550 millisecond range in the EP response is performed substantially as described with respect to FIG. 26 in the previously mentioned related application. Once the EPs for the correct and incorrect answers are determined, the difference between the peak voltage level in the 300–500 msec range for the correct answer EP and the peak voltage level in the 300–500 msec range for the incorrect answer EP is computed. This difference is larger for students with greater understanding of the training material and smaller for students with less understanding of the training material.

The recording of the EEG data is performed as described in the previously mentioned related U.S. patent application and is described in detail with respect to FIG. 22 therein. However, the calculation of the amplitudes of the alpha and beta components of the recorded EEG signal is performed in a different manner than as described in the above-mentioned related U.S. patent application.

Figure 8:
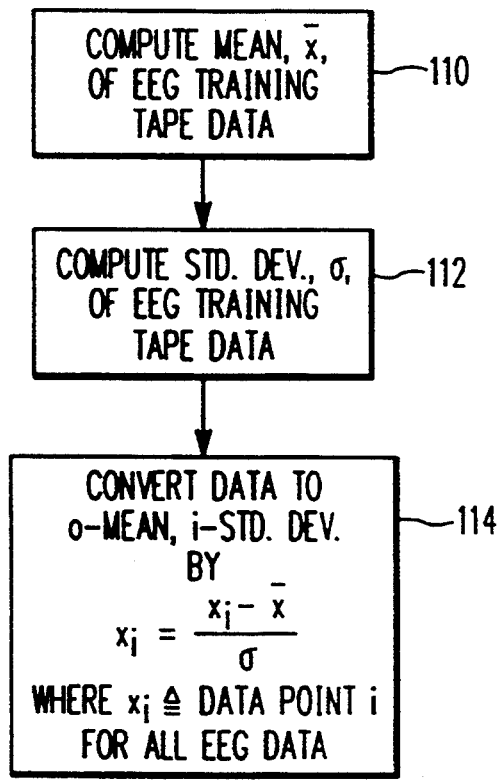
FIG. 8 depicts how the EEG data is normalized.
Figure 7:
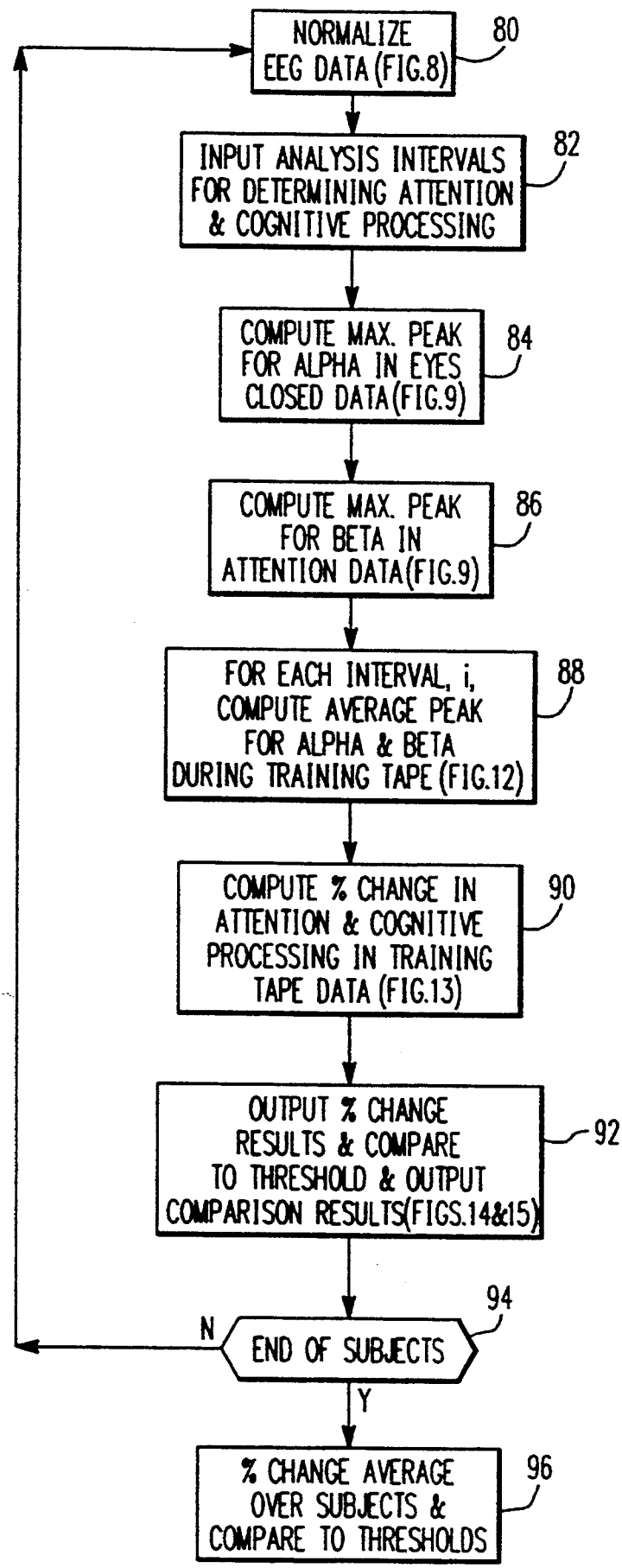
FIG. 7 illustrates the general operations for processing the EEG data.

As previously mentioned EEG data for obtaining a baseline is collected to determine alpha and beta baselines while the student has their eyes closed and while they are engaged in a cognitive activity such as counting backward. The time interval during which the baseline data is recorded, is preferably 30 seconds although a time interval between 30 seconds and 60 seconds is appropriate. Once the baseline data is recorded, the EEG is recorded during the training tape. The first step during processing, is illustrated in FIG. 7, is to normalize 80 the EEG data. The normalization operation will be described in more detail with respect to FIG. 8, however, it involves computing the standard deviation and the mean of the EEG training data and then mapping the raw EEG data to a zero mean and one standard deviation by subtracting the mean from each data point and dividing the result by the standard deviation. This will be discussed in more detail with respect to FIG. 8. Next, the time intervals for analysis are input 82. These intervals have a start time and a width and designate the data for which analysis is desired. For example, the evaluation may only be desired for a single small segment of the training material and only the corresponding portion of the EEG data needs to be analyzed. These time intervals can range from a minimum of 0.5 seconds up to the entire length of the training material. Next, the system determines the baseline levels for low attention and low cognitive processing by computing 84 the maximum peak in the alpha during the data and computing 86 the maximum peak in the beta during the thinking data. The maximum peak computation operations will be discussed in more detail with respect to FIG. 9. Then, the system computes 88 the average alpha and beta peaks for the training tape data for each interval previously specified. This operation will be discussed in more detail with respect to FIG. 12. The system then determines 90 a percent change in the attention and cognitive processing levels in the training tape data which will be discussed in more detail with respect to FIG. 13. The percent change results are output 92 and used to compare against the thresholds which will indicate whether the subject has learned the subject matter. How these thresholds are determined will be described with respect to FIGS. 14 and 15. The system then tests 94 to determine whether the EEG data for all of the subjects tested has been processed. If not, a loop-back occurs to process the remaining subjects' data. If all of the subjects have been processed, then the average percent change over the subjects is computed and output. This average percent change is also compared to an average threshold to determine the overall learning promoted by the training material.

Normalizing 88 the data involves (FIG. 8) a conventional mean computation 110 followed by a conventional standard deviation computation 112. Once the mean and standard deviation are computed, the raw data is converted 114 into normalized data as illustrated FIG. 8.

Figure 9:
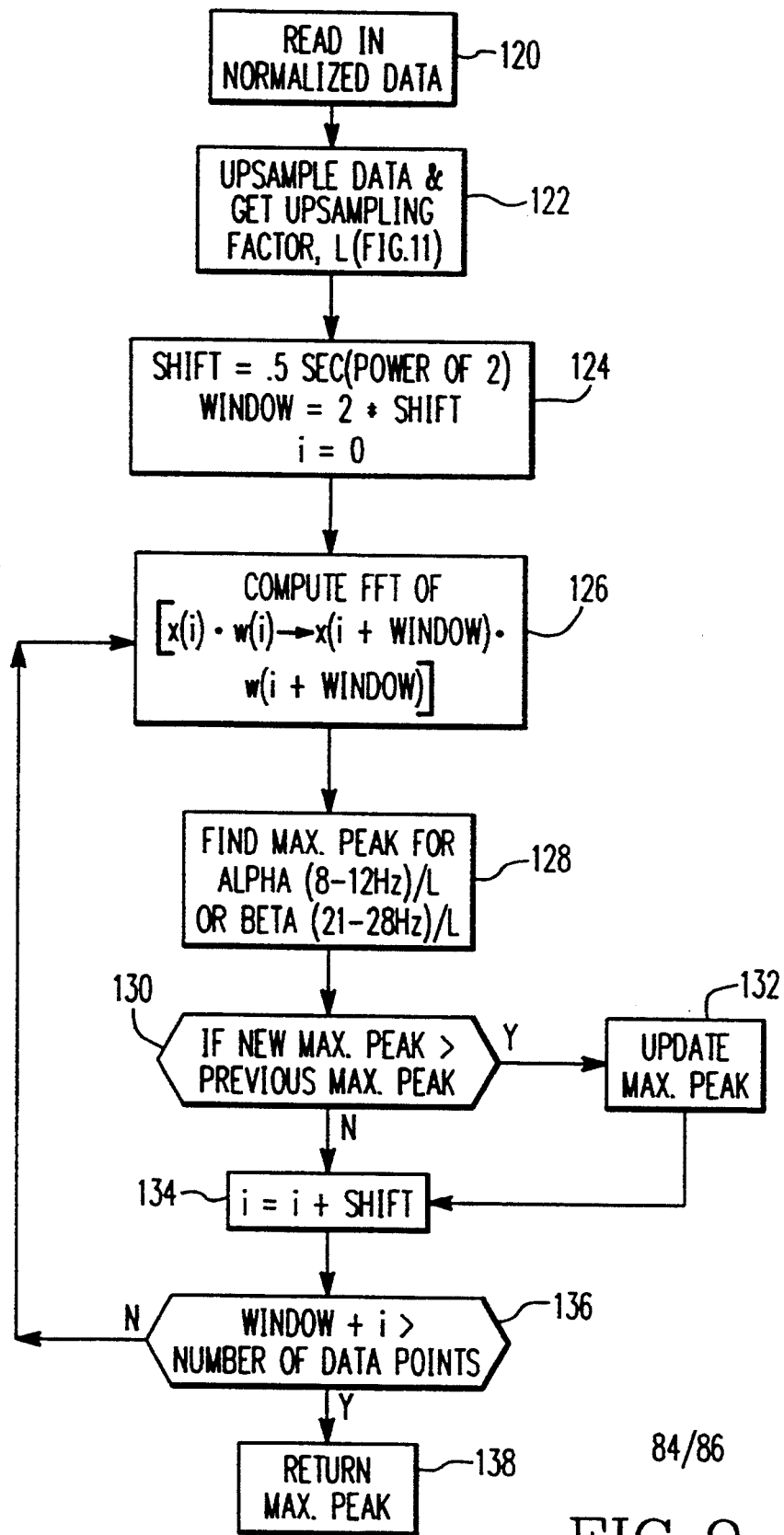
FIG. 9 illustrates peak detection.

The maximum peak computations in steps 84 and 86 of FIG. 7 are illustrated in detail in FIG. 9. This operation involves reading 120 the normalized data and upsampling (interpolating) the data to create data at a higher sampling rate and to obtain an upsampling factor. This step will be discussed in more detail with respect to FIGS. 10 and 11. Next, control parameters associated with the amount of shift and the size of the window used during the following computations are set 124. The system then windows the data using a minimum Three Term Blackman Harrison window and then performs an FFT on $2^n$ point windowed segments of the data with overlapping windows of $2^n/2$ points. For example, if $2^n = 512$, the first window for the FFT is for data points 0 to 512. The second window for points 256 to 768, the third window includes points 512 to 1024 and the fourth window points 768 to 1280. Next the system finds the maximum peak in the alpha frequency band or the beta frequency band (depending on whether this is step 84 or 86) after the frequency data is shifted by dividing by the upsampling factor L. This division by L adjusts the frequency scale in the average spectrum to account for the upsampling performed in step 122. The maximum peak is found 130 by simply comparing the old peak to the new peak and if the new peak is higher than the old peak, then the system saves 132 the new peak as the maximum peak. The system then performs the appropriate shift 134. A test is then performed 136 to determine whether the last window has been processed and if so the maximum peak found is returned.

Figure 10:
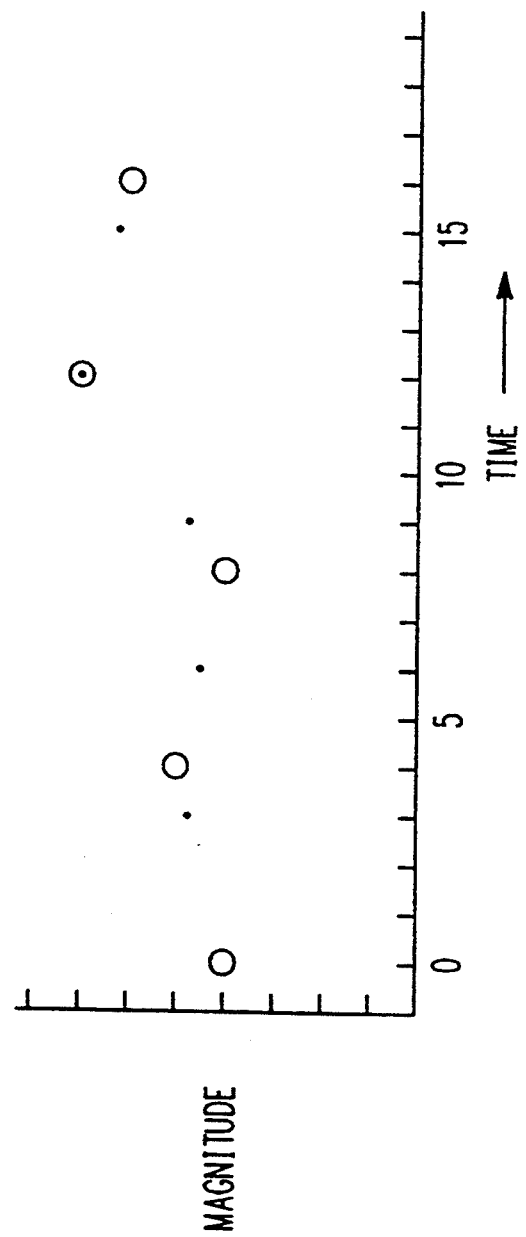
FIG. 10 is a graph showing how upsampling occurs.
Figure 11:
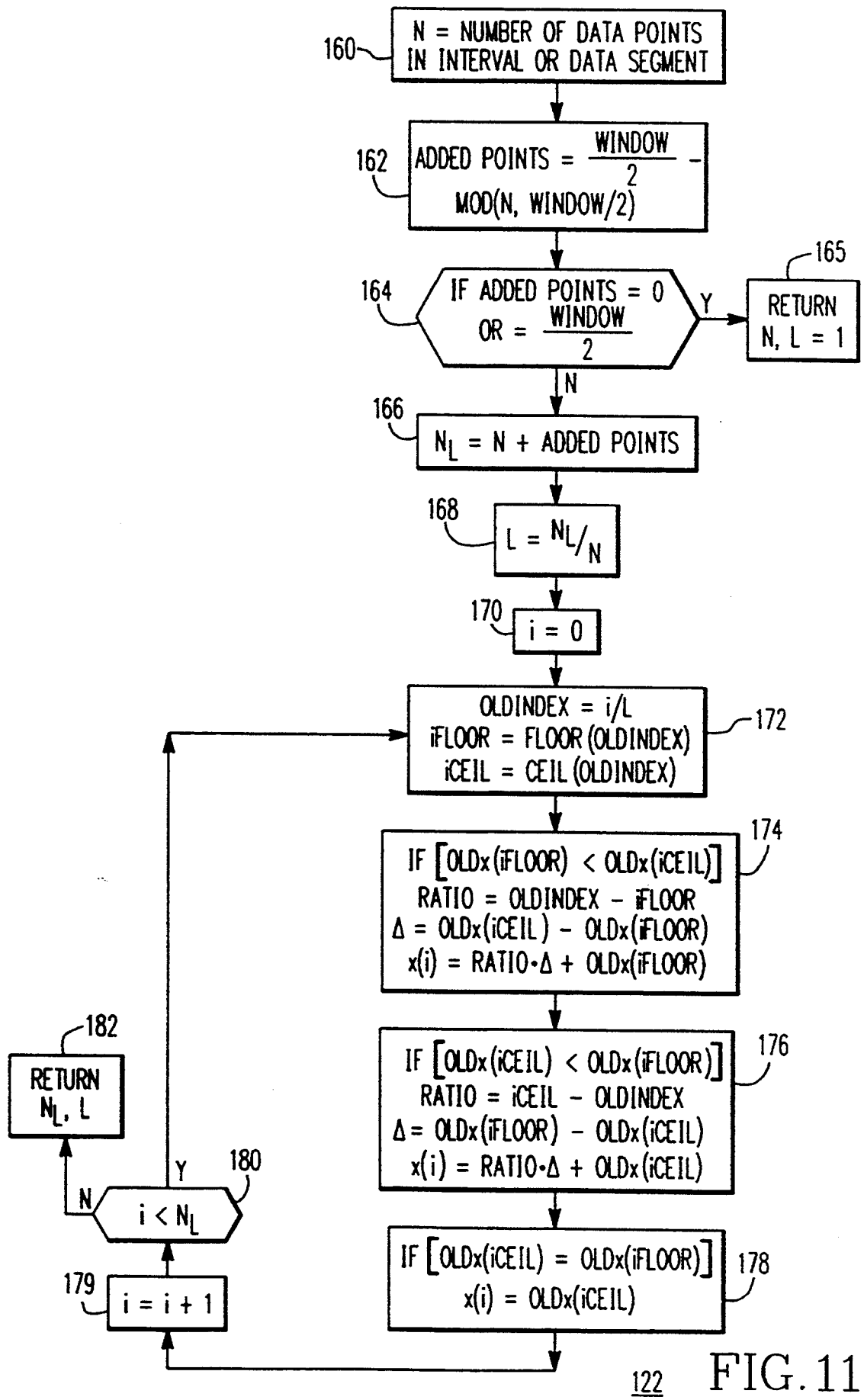
FIG. 11 illustrates the steps performed during upsampling.

The upsampling operation 122 and how it is performed is illustrated in FIGS. 10 and 11. In general the system finds the smallest number, N, that is greater than or equal to the number of actual data points and is also divisible by half of the window length size $2^n$, where n is a positive integer. The system then performs upsampling on the data by interpolating the data from the actual number of data points to N data points. The upsampling factor L is N divided by the actual number of data points. In FIG. 10 the original normalized EEG data is shown by circles and the new or substitute data is shown by dots. As can be seen, the original data is sampled every four time units and the upsampled data is provided every three time units. That is a four to three conversion is performed. As graphically illustrated in FIG. 10, a simple linear interpolation is performed to find the new data value at any new data value point located between actual data points. In particular as illustrated in FIG. 11, the system determines 160 the number N of data points in the interval or data segment. The number of points that need to be added is then computed 162 as illustrated. Next, a test 164 is performed to determine whether the number of points that need to be added is zero. If so, the number of data points N is returned and the upsampling factor L is set to 1. Otherwise the number of new points is determined 166 and used to determine 168 the interpolation factor. Next, a pointer index is set 170 followed by entry into a loop 172–182 that performs the interpolation by creating a new data array of new data and substituting the new data array for the old data array and returning the substituted data array, the new number of data points N and the upsampling factor L.

Figure 12:
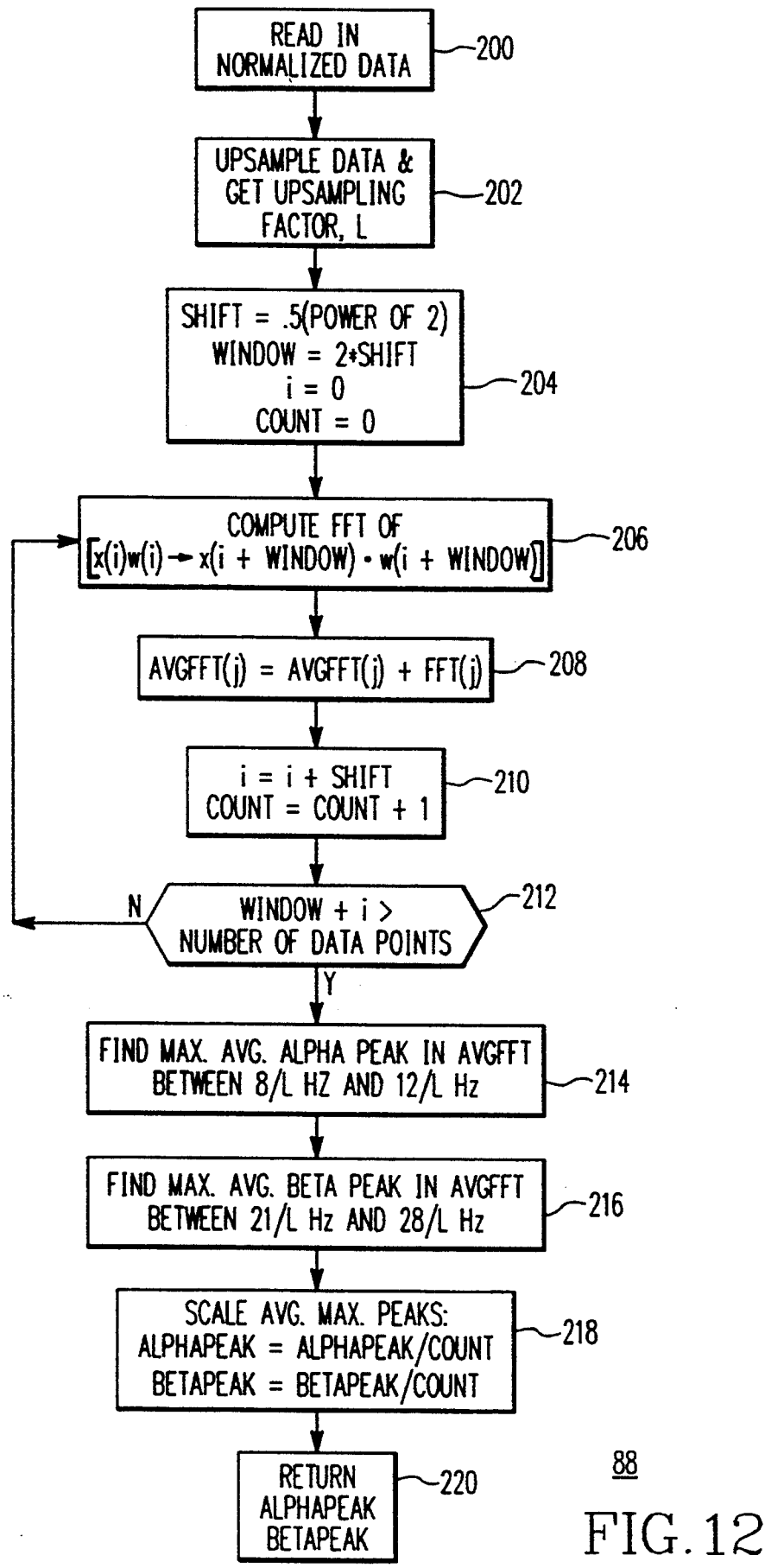
FIG. 12 is a flowchart showing average computations.

When the average peak is computed 88 in the training tape data, as illustrated in FIG. 12, the system reads 200 the normalized data and upsamples the data as described previously with respect to FIG. 11. Like the computation of the maximum peak described with respect to FIG. 9, the system sets 204 processing parameters and computes 206 an FFT using a Three Term Blackman Harrison window. An average FFT is then computed 208. The average computation is then followed by an update 210 of the shift variable and a count variable. Once the parameters are updated, a determination 212 is made concerning whether the end of the data points have been reached. If so, the maximum average peak in the alpha data is found 214 by scanning for the peak in the adjusted frequency range. The same scanning operation is performed 216 with respect to the beta data. Next, the system scales 218 the peaks and returns 220.

Figure 13:
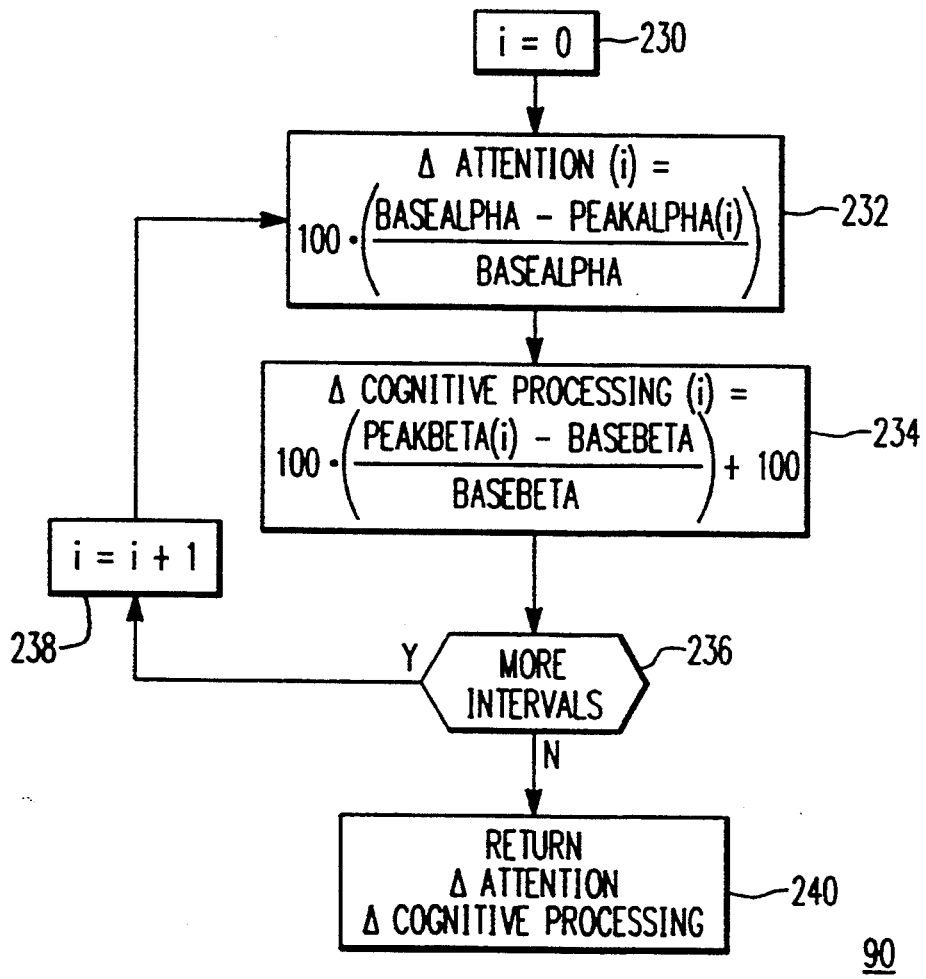
FIG. 13 illustrates percent change computations.

As illustrated in FIG. 13, the computation 90 of the percent change in the attention and cognitive processing levels starts by setting 230 a pointer and then entering a loop in which the percent change in the alpha activity is computed 232 and then the beta activity 234 is computed. The system then determines 236 whether additional intervals of data need to be processed and if so, updates 238 the interval pointer. If not, the system returns to 240 the percent changes.

Figure 14:
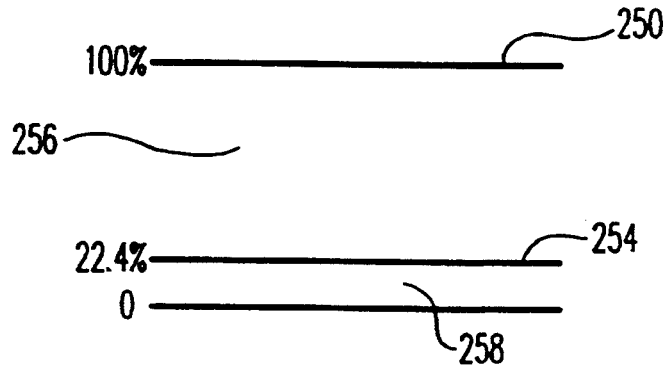
FIGS. 14 and 15 depict threshold determinations using the percent change.
Figure 15:
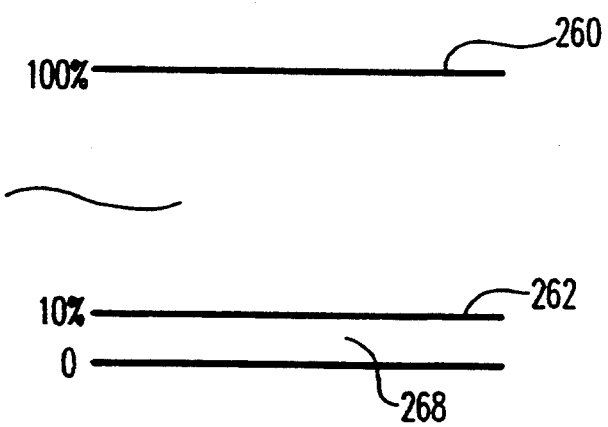

The step of comparing 92 the percent change to a threshold uses a threshold for the beta data and the alpha data which is determined as illustrated in FIGS. 14 and 15. The beta baseline 250 is the level of the beta activity recorded during the baseline cognitive process previously mentioned, such as counting backwards. The threshold beta level 254 is set at 22.4% of the baseline beta level 250. Any beta activity level greater than 22.4% of the baseline occurs in the region 256 and is considered to be a high cognitive level. Beta activity in this region 256 is negatively correlated to understanding the subject matter. Any beta activity level less than 22.4% of the baseline occurs in region 258 and is considered to be a low cognitive level which is indicative of learning the subject matter. The alpha nonattention baseline (highest alpha) 260 illustrated in FIG. 15 is used to compute a learning threshold 262. The threshold 262 is 10% of the nonattention baseline level 260 which is the attention level measured when the eyes are closed and no backward counting occurs. If the alpha activity of the recorded EEG during training moves into the region 266, this activity would be considered a low attention level indicative of not learning. If the alpha activity during training is in region 268 (less than 10% of the nonattention baseline 260), it is indicative of learning.

The many features and advantages of the invention are apparent from the detailed specification and thus it is intended by the appended claims to cover all such features and advantages of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method of evaluating training material, comprising the steps of:
   (a) measuring nonattention and cognitive baselines;
   (b) presenting the training material to a subject and recording the electroencephalographic (EEG) activity of the subject; and
   (c) measuring one of an attentive level and a cognitive level of the subject using the EEG activity by comparing the attention level and the cognitive level to attention and cognitive thresholds, where one of high attention levels and low cognitive levels indicate effective training material, where one of the attention level above the attention threshold and the cognitive level below the cognitive threshold indicates effective training material and where the attention threshold is 0.10 of the nonattention baseline and the cognitive threshold is 0.244 of the cognitive baseline.

2. A method of evaluating videotaped training material, comprising the steps of:
   (a) presenting the videotaped training material to a subject and recording the electroencephalographic (EEG) activity of the subject during the presentation;
   (b) measuring an attention level and a cognitive level of the subject using EEG alpha and beta activity of comparing the attention level and the cognitive level to attention and cognitive thresholds, where the attention level above the attention threshold and the cognitive level below the cognitive threshold indicates effective training material, the attention and cognitive thresholds are determined by measuring baselines and the attention threshold is 0.10 of a nonattention baseline and the cognitive threshold is 0.244 of a cognitive baseline;
   (c) presenting a multiple choice question to the subject on the training material followed by usually presenting incorrect and correct answers;
   (d) measuring evoked potentials produced by the subject when the correct and incorrect answers are presented; and
   (e) comparing the evoked potentials for the correct and incorrect answers, where an evoked potential for a correct answer having an amplitude higher than for an incorrect answer indicates effective training material.

3. A method of electroencephalographic (EEG) spectral estimation, comprising the steps of:
   (a) normalizing EEG data;
   (b) upsampling the EEG data to a number of data points N evenly divisible by $2^n$ where n is a positive integer and determining an interpolation factor;
   (c) performing a three term window FFT with overlapping windows to obtain an EEG spectrum; and
   (d) adjusting the EEG spectrum using the interpolation factor.

4. A method as recited in claim 3, further comprising the steps of:
   (e) determining a peak for a frequency range of the EEG spectrum.

5. A method as recited in claim 3, wherein step (c) includes averaging spectra of the overlapping windows.

6. A method as recited in claim 3, further comprising (e) obtaining a peak in the spectrum.

7. A method as recited in claim 6, wherein the peak is one of an average peak and a maximum peak.

* * * * *